(12) United States Patent
Yaegashi et al.

(10) Patent No.: US 8,247,591 B2
(45) Date of Patent: Aug. 21, 2012

(54) NANOPARTICLE AND NANOPARTICLE COMPOSITE

(75) Inventors: Hideaki Yaegashi, Kanagawa (JP); Shoko Kano, Kanagawa (JP); Masahiko Yamanaka, Kanagawa (JP); Kentarou Watanabe, Kanagawa (JP); Hiroshi Yokoyama, Kanagawa (JP); Hideo Sawada, Aomori (JP)

(73) Assignee: Nissan Motor Co., Ltd., Yokohama-shi (JP)

( * ) Notice: Subject to any disclaimer, the term of this patent is extended or adjusted under 35 U.S.C. 154(b) by 120 days.

(21) Appl. No.: 12/910,739

(22) Filed: Oct. 22, 2010

(65) Prior Publication Data

US 2011/0040024 A1 Feb. 17, 2011

Related U.S. Application Data

(62) Division of application No. 11/715,496, filed on Mar. 8, 2007, now Pat. No. 7,825,283.

(30) Foreign Application Priority Data

Sep. 13, 2006 (JP) ................................ 2006-248075

(51) Int. Cl.
*C07F 7/21* (2006.01)
*C07F 7/10* (2006.01)

(52) U.S. Cl. ........ 556/460; 556/411; 556/419; 556/420; 556/434; 556/400

(58) Field of Classification Search .................. 556/400, 556/460, 411, 419, 420, 434
See application file for complete search history.

(56) References Cited

U.S. PATENT DOCUMENTS

| | | | |
|---|---|---|---|
| 6,387,453 B1 | 5/2002 | Brinker et al. |
| 6,558,455 B2 | 5/2003 | Sammons et al. |
| 6,645,569 B2 | 11/2003 | Cramer et al. |
| 6,818,760 B1 | 11/2004 | Spicer et al. |
| 7,378,103 B2 | 5/2008 | Kanji et al. |
| 2007/0172673 A1 | 7/2007 | Becker et al. |

OTHER PUBLICATIONS

H. Sawada et al., "Solubilization of fullerene into ionic liquids by the use of fluoroalkyl end-capped oligomers," Polymers for Advanced Technologies, vol. 16, 2005, pp. 655-658.

H. Sawada et al., "Solubilization of fullerene into water with fluoroalkyl end-capped amphiphilic oligomers—novel fluorescence propeties," Journal of Colloid and Interface Science 263 (2003), pp. 1-3.

H. Sawada, "Construction of Nano-level Structure-controlled Fluorine-based Molecule Aggregate and Coating Surface Improvement," Science Council of Japan, 11th Interface Symposium, (2004), pp. 63-85.

Notice of Allowance in U.S. Appl. No. 11/715,496 dated Jun. 23, 2010.

Sawada et al., "Preparation of novel fluoroalkyl end-capped oligomers/silica hybrid nanoparticles-encapsulation of a variety of guest molecules into fluorinated nanoparticles", Colloid & Polymer Science, Feb. 2006, vol. 284, No. 5, pp. 551-555.

U.S. Appl. No. 11/715,495, filed Mar. 8, 2007.

*Primary Examiner* — Elvis O Price

(74) *Attorney, Agent, or Firm* — Foley & Lardner LLP

(57) ABSTRACT

A nanoparticle includes a chain oligomer section having a hydrophilic group and fluoroalkyl groups respectively at its opposite terminals, a three-dimensional silica network section, and an organic chain having fluorine or silicon, and is represented by the following formula (2):

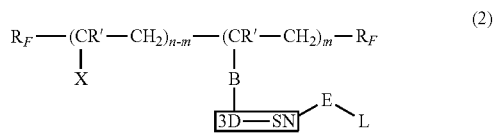

where R' is independent H or independent alkyl group; X is the hydrophilic group and is selected from the group consisting of an OH group, an NCO group, an $NH_2$ group, an NHR group (where R is alkyl group) and a COY group (where Y is a hydrophilic group); $R_F$ is the fluoroalkyl group having a carbon number of 2 to 10 and a molecular weight of 119 to 1000; 3D-SN is the three-dimensional silica network section; B is selected from the group consisting of an O, O=C—O, NH—C=O and NR—C=O (where R is alkyl group); E is O, O=C—O, NH—C=O or NR—C=O (where R is alkyl group); L is $(CH_2O)_l$—$[Si(CH_3)_2O]_k$—$(CH_2O)_l$-α, $(CF_2)$j-α or $(CF_2O)_h$-α where α is COY group (where Y is hydrophilic group), NCO group, $NH_2$ group, NHR group (R is alkyl group), R group (or alkyl group) or H; n is $1 \leq n \leq 10$; m is $1 \leq m \leq n$; k is $1 \leq k \leq 500$; l is $0 \leq l \leq 10$; j is $0 \leq j \leq 20$; and h is $1 \leq h \leq 20$.

4 Claims, No Drawings

NANOPARTICLE AND NANOPARTICLE COMPOSITE

This application is a division of application Ser. No. 11/715,496, filed Mar. 8, 2007, which claims priority to Japanese Patent Application No. 2006-248075, filed Sep. 13, 2006, both of which are hereby incorporated be reference in their entirety.

BACKGROUND OF THE INVENTION

This invention relates to a new nanoparticle and a nanoparticle composite, and more particularly to the nanoparticle which can improve the dispersibility and surface orientation of guest molecule, and the nanoparticle composite in which the guest molecule is included in the nanoparticle.

In conventional techniques, a compound having a long chain alkyl group such as an acrylic ester oligomer or the like is slightly soluble in a solvent because molecules are entangled with each other. Against this, it has been found to reduce such cohesion and to increase the solubility by using the fact that the surface energy of fluorine is low. However, this is insufficient in orientation to the surface of solvent and resin (See, for example, Non-patent literatures 1 to 3).

[Non-patent literature 1] H. Sawada, R. Kasai et al., polym. Adv. Tech., 16, 655 (2005);

[Non-patent literature 2] H. Sawada, J. Iidzuka et al., J. Colloid Interface Sci., 263, 1 (2003); and

[Non-patent literature 3] Science Council of Japan, 11$^{th}$ Interface Symposium "Construction of Nano-level Structure-controlled Fluorine-based Molecule Aggregate and Coating Surface Improvement", Hirosaki University, Hideo Sawada (2004).

SUMMARY OF THE INVENTION

In such conventional techniques, if an oligomer having fluoroalkyl groups respectively at its opposite terminals is used, the dispersibility into the solvent of a binder resin and a surface orientation characteristics are improved. However, according to kinds of resins to be used, it occurs frequently that the surface orientation characteristics is degraded owing to an interaction between the resin and the oligomer having fluoroalkyl groups respectively at its opposite terminals.

Additionally, it has been known that the surface orientation characteristics is further improved if the oligomer having fluoroalkyl groups respectively at its opposite terminals is formed into a nano-composite by using silica. However, even in this case, there has been encountered such a problem that the orientation characteristics to the solvent and the resin surface is degraded so that the composite unavoidably remain inside a resin film and therefore the amount of the composite existing at the surface of the resin film becomes small.

An object of the present invention is to provide an improved nanoparticle and a nanoparticle composite which can effectively solve the problems encountered in conventional techniques.

Another object of the present invention is to provide an improved nanoparticle which has a function as host molecule and can improve the dispersibility and surface orientation characteristics of guest molecule, and nanoparticle composite in which the guest molecule is included in the nanoparticle.

In order to attain the above-mentioned objects, the present inventors have eagerly made many studies. As a result, they have found that the above-mentioned objects can be attained by introducing a certain organic chain which can improve the orientation characteristics to a solvent and a resin surface, thus reaching the completion of the present invention.

In other words, a nanoparticle according to the present invention comprises a chain oligomer section having a hydrophilic group and fluoroalkyl groups respectively at its opposite terminals, a three-dimensional silica network section, and an organic chain having fluorine or silicon, and has a structure represented by the following formula (1):

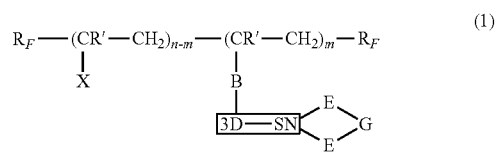

where R' is independent H or independent alkyl group; X is the hydrophilic group and is independent OH group, independent NCO group, independent $NH_2$ group, independent NHR group (where R is alkyl group) or independent COY group (where Y is hydrophilic group); $R_F$ is the fluoroalkyl group having a carbon number of 2 to 10 and a molecular weight of 119 to 1000; 3D-SN is the three-dimensional silica network section; B is independent O, independent O=C—O, independent NH—C=O or independent NR—C=O (where R is alkyl group); E is O, O=C—O, NH—C=O or NR—C=O (where R is alkyl group); G is $[(CH_2O)_l$—$[Si(CH_3)_2O]_k$, $(CH_2O)_l]$, $(CF_2)j$ or $(CF_2O)_h$; n is $1 \leq n \leq 10$; m is $1 \leq m \leq n$; k is $1 \leq k \leq 500$; l is $0 \leq l \leq 10$; j is $0 \leq j \leq 20$; and h is $1 \leq h \leq 20$; or the following formula (2)

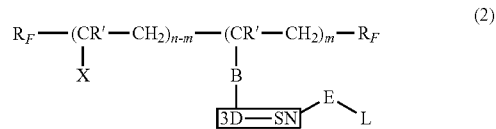

where R' is independent H or independent alkyl group; X is the hydrophilic group and is independent OH group, independent NCO group, independent $NH_2$ group, independent NHR group (where R is alkyl group) or independent COY group (where Y is a hydrophilic group); $R_f$ is the fluoroalkyl group having a carbon number of 2 to 10 and a molecular weight of 119 to 1000; 3D-SN is the three-dimensional silica network section; B is independent O, independent O=C—O, independent NH—C=O or independent NR—C=O (where R is alkyl group); E is O, O=C—O, NH—C=O or NR—C=O (where R is alkyl group); L is $[(CH_2O)_l$—$[Si(CH_3)_2O]_k$—$(CH_2O)_l]$-$\alpha$, $(CF_2)j$-$\alpha$ or $(CF_2O)_h$-$\alpha$ where $\alpha$ is COY group (where Y is hydrophilic group), NCO group, $NH_2$ group, NHR group (R is alkyl group), R group (or alkyl group) or H; n is $1 \leq n \leq 10$; m is $1 \leq m \leq n$; k is $1 \leq k \leq 500$; l is $0 \leq l \leq 10$; j is $0 \leq j \leq 20$; and h is $1 \leq h \leq 20$.

Additionally, the nanoparticle composite according to the present invention includes a host molecule which is the above-mentioned nanoparticle, and a guest molecule included in this host molecule.

DETAILED DESCRIPTION OF THE INVENTION

Hereinafter, a formed product according to the present invention will be discussed in detail. In the specification and the claims of the present application, "%" for concentration, filling amount, blending amount or the like represents % by mass unless otherwise specified. Additionally, or "nanoparticle" or "nanoparticle composite" means typically a particle or a composite of the nano-order in size; however, it is unnecessary to be of the nano-order and therefore includes ones having particle sizes of about 0.5 nm to about 1 μm.

A nanoparticle according to the present invention has a function as a host molecule and comprises a chain oligomer section having a hydrophilic group and fluoroalkyl groups respectively at its opposite terminals, a three-dimensional (3D) silica network (SN) section, and an organic chain having fluorine or silicon.

Here, the above-mentioned chain oligomer section accomplishes the function of orientation to a solvent or a resin surface. The 3D silica network has a three-dimensional network structure with siloxane linkage (—Si—O-)n and accomplishes the function of including a guest molecule. The organic chain having fluorine or silicon is typically originated from polysiloxane or fluoroalcohol and accomplishes the function of further improving the orientation characteristics to a solvent or a resin surface.

Additionally, the nanoparticle according to the present invention has a structure represented by the following formula (1):

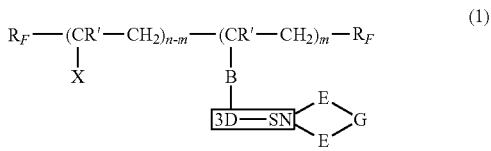

where R' is independent H or independent alkyl group; X is the hydrophilic group and is independent OH group, independent NCO group, independent $NH_2$ group, independent NHR group (where R is alkyl group) or independent COY group (where Y is hydrophilic group); $R_F$ is the fluoroalkyl group having a carbon number of 2 to 10 and a molecular weight of 119 to 1000; 3D-SN is the three-dimensional silica network section; B is independent O, independent O=C—O, independent NH—C=O or independent NR—C=O (where R is alkyl group); E is O, O=C—O, NH—C=O or NR—C=O (where R is alkyl group); G is $[(CH_2O)_l$—$[Si(CH_3)_2O]_k$—$(CH_2O)_l]$, $(CF_2)j$ or $(CF_2O)_h$; n is $1\leq n\leq 10$; m is $1\leq m\leq n$; k is $1\leq k\leq 500$; l is $0\leq l\leq 10$; j is $0\leq j\leq 20$; and h is $1\leq h\leq 20$; or the following formula (2):

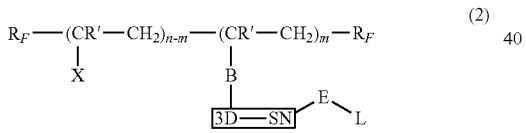

where R' is independent H or independent alkyl group; X is the hydrophilic group and is independent OH group, independent NCO group, independent $NH_2$ group, independent NHR group (where R is alkyl group) or independent COY group (where Y is a hydrophilic group); $R_F$ is the fluoroalkyl group having a carbon number of 2 to 10 and a molecular weight of 119 to 1000; 3D-SN is the three-dimensional silica network section; B is independent O, independent O=C-0, independent NH—C=O or independent NR—C=O (where R is alkyl group); E is O, O=C—O, NH—C=O or NR—C=O (where R is alkyl group); L is $[(CH_2O)_l$—$[Si(CH_3)_2O]_k$—$(CH_2O)_l]$-α, $(CF_2)j$-α or $(CF_2O)_h$-α where α is COY group (where Y is hydrophilic group), NCO group, $NH_2$ group, NHR group (R is alkyl group), R group (or alkyl group) or H; n is $1\leq n\leq 10$; m is $1\leq m\leq n$; k is $1\leq k\leq 500$; l is $0\leq l\leq 10$; j is $0\leq j\leq 20$; and h is $1\leq h\leq 20$.

Y (or hydrophilic group) in X in the formulae (1) and (2) is not particularly limited and is suitably selected from, for example, functional groups (hydroxyl group, morpholine group, N-(1,1-dimethyl-3-oxobutyl)amino group and dimethylamino group) which are respectively independent and represented by formulae (3) to (6), sulfone group and amino group other than the above-mentioned. It is to be noted that Y may not be of the same kind in the same oligomer molecule.

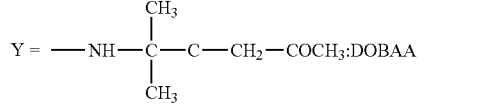

A typical structure of the 3D-SN section in the formulae (1) and (2) will be schematically shown, in which the structures shown in the formulae (1) and (2) are represented respectively by the following formulae (7) and (8):

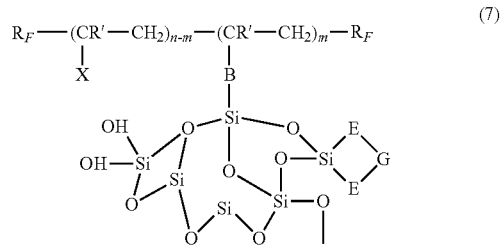

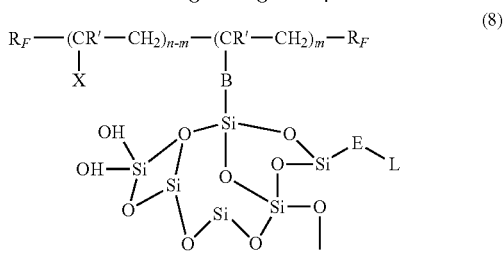

As typical examples of the nanoparticle according to the present invention, there are ones represented by the following formula (9) and (10):

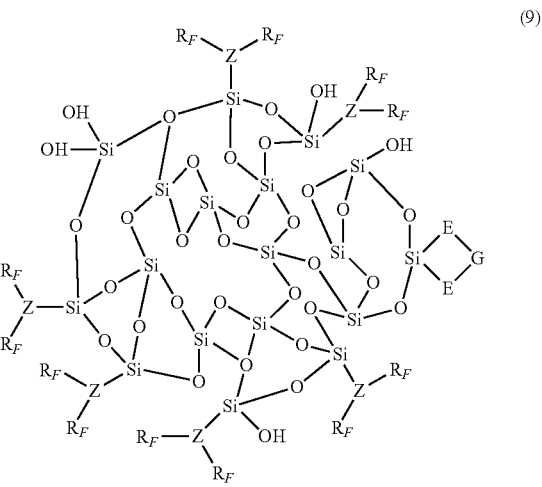

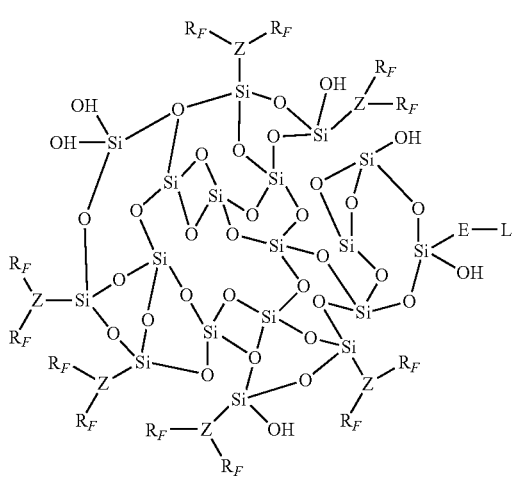

(10)

It is to be noted that, in the formula (9) or (10), $R_F$, E, G and L respectively represent ones corresponding to those in the above-mentioned, and Z is represented by the following formula (11) or (12):

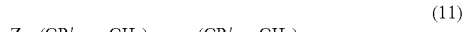
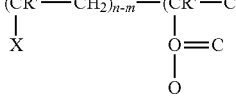

(11)

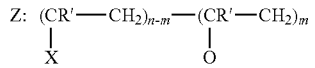

(12)

It is to be noted that, in the formula (11) or (12), R', $R_F$, E, G, L, m, n, k, l, j and h respectively represent ones corresponding to those in the above-mentioned.

In the nanoparticle according to the present invention, the chain oligomer section having the hydrophilic group (X) and the fluoroalkyl groups ($R_F$) at its opposite terminals is originated from an oligomer (where R', $R_F$, X, m and n respectively represent the same ones as in the above-mentioned) represented by the following formula (13).

In this nanoparticle, it is preferable that the molecular weight of the oligomer section is 252 to 100,000 upon being calculated in terms of the oligomer of the formula (13).

In case that the molecular weight is less than 252 or exceeds 100,000, it may not be applied to the present invention.

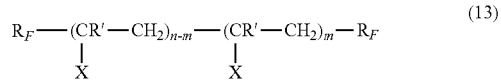

(13)

Next, the nanoparticle composite according to the present invention will be discussed.

As discussed above, the nanoparticle composite according to the present invention includes the guest molecule included in the host molecule which is the above-mentioned nanoparticle composite.

Here, the guest molecule is not particularly limited, in which examples of the guest molecule are carbon nanotube, carbon nanohorn, HIV virus, fullerene, magnetic particle (magnetite particle), gold particle, silver particle, nanodiamond particle, hibitane, fluorescein and the like. Further, by-product carbon particle in production of fullerene, known as a functional material can be also used as the guest molecule.

Additionally, in the nanoparticle composite according to the present invention, the above-mentioned 3D-SN section is cross-linked with tetraethoxysilane (TEOS) thereby making it possible to construct addition of the chain oligomer having the hydrophilic group and the fluoroalkyl groups respectively at opposite terminals and of the organic chain having fluorine or silicon.

Particularly, this is particularly effective for the nanoparticle composite in which the guest molecule is included in the nano particle (the host molecule) having the structure represented by the formula (9) or (10), by which a high surface orientation of the guest molecule can be obtained.

Since the above-mentioned nanoparticle (the host molecule) has an excellent dispersibility, the nanoparticle composite according to the present invention has the same advantage thereby making it possible to cause a variety of guest molecules to be well dispersed and surface-oriented.

Accordingly, for example, by exposing a specified guest molecule at a surface, it is possible to cause the guest molecule to effectively exhibit its characteristics.

Hereinafter, production methods of the above-mentioned nanoparticle and nanoparticle composite will be discussed.

(Production method of oligomer having fluoroalkyl groups respectively at its opposite terminals and hydrophilic group in its main chain)

[Production of Perfluoroaryl Chloride]

Anhydrous perfluorocarboxylic acid ($RFCO_2H$) and benzoil chloride (PhCOCl) were mixed in a rate of 1:2 mmol and then rapidly heated at the boiling point of the anhydrous perfluorocarboxylic acid or a temperature slightly higher than the boiling point and cooled to a room temperature. The obtained crude product was subjected to a fractional distillation to be purified thereby obtaining perfluoroaryl chloride ($R_FCOCl$).

For example, in case that $CF_3CF_2CF_2CO_2H$ is used as anhydrous perfluorocarboxylic acid ($R_FCO_2H$), the yield of $CF_3CF_2CF_2COCl$ is 70%; in case that the yield of $CF_3CF_2CF_2CF_2CF_2CF_2CF_2CO_2H$ is used as anhydrous perfluorocarboxylic acid, the yield of $CF_3CF_2CF_2CF_2CF_2CF_2CF_2COCl$ is 77%; in case that $HCF_2CF_2CO_2H$ is used as anhydrous perfluorocarboxylic acid, the yield of $HCF_2CF_2COCl$ is 71%; in case that $HCF_2CF_2CF_2CF_2CO_2H$ is used as anhydrous perfluorocarboxylic acid, the yield of $HCF_2CF_2CF_2CF_2COCl$ is 70%, thus obtaining the perfluoroaryl chloride as an object.

[Production of Fluoroalkanoyl Peroxide]

Into a sufficient amount of a nonpolar fluorine solvent (Freon-113; $CF_2ClCFCl_2$) which is kept at −5° C. to −7° C., first a sodium hydroxide aqueous solution prepared by dissolving NaOH at a rate of 0.12 g per 1 ml of water is added; subsequently a 30% hydrogen peroxide aqueous solution is added and a quick stirring is made; and thereafter $R_FCOCl$ which has been previously cooled at −5° C. to −7° C. is added and then stirring is made for 2 minutes, so that RFCOCl, NaOH and $H_2O_2$ are contained respectively at 1:1:0.5 in mol ratio.

Thereafter, the temperature is slightly raised (however, to not higher than 0° C.), and then allowing to stand is made after stirring for 6 to 7 minutes is made. Then, an oily layer is extracted from two separate oily and aqueous layers thereby obtaining fluoroalkanoyl peroxide (($R_FCOO)_2$) as an objective product. It is to be noted that it is preferable to rinse the product with a saturated sodium hydrogencarbonate which has been cooled by ice.

Here, perfluoroaryl chloride used for fluoroalkanoyl peroxide may be replaced with a halide compound such as perfluoroaryl fluoride, perfluoroaryl bromide or the like, as represented by the following formula (14);

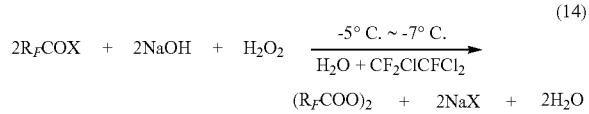

where $R_f$: fluoroalkyl group, X: halogen (Production Method of Oligomer Having Fluoroalkyl Groups Respectively at its Opposite Terminals and Hydrophilic Group in its Main Chain)

Fluoroalkanoyl peroxide, for example, perfluoro-2-methyl-3-oxohexanoyl peroxide in an amount of 5 mmol is added to 35 g of fluorine-based solvent (AK-225 which is a mixture solvent (1:1) of 1,1-dichloro-2,2,3,3,3-pentafluoropropane and 1,3-dichloro-1,2,2,3,3-pentapentafluoropropane). To this solution, a mixture solution of 24 mmol of a monomer having hydrophilic group, for example, acryloylmorpholine (=ACMO) and 50 g of the fluorine-based solvent (AK-225) is added, and then stirring is made at 45° C. for 5 hours in a nitrogen atmosphere. After the stirring, the solvent is evaporated thereby obtaining 4.55 g of bis(perfluoro-1-methyl-2-oxapentylated) ACMO oligomer.

The reaction formula of the above is shown as the following formula (15):

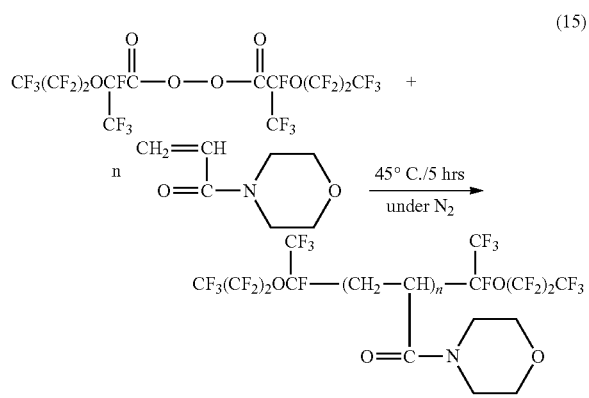

Additionally, as the oligomer having the fluoroalkyl groups respectively at its opposite terminals and the hydrophilic group in its main chain, the following compounds other than the above-mentioned ones may be used as fluoroalkanoyl peroxide: for example, $(CF_3CF_2CF_2COO)_2$, $(CF_3CF_2CF_2CF_2CF_2CF_2CF_2COO)_2$, $(HCF_2CF_2COO)_2$, $(HCF_2CF_2CF_2CF_2COO)_2$, $(HCF_2CF_2CF_2CF_2CF_2COO)_2$, $(C_3F_7OCF(CF_3)CF_2OCF(CF_3)COO)_2$, $(C_3F_7OCF(CF_3)COO)_2$, and the like. As the monomer having the hydrophilic group, for example, N,N-dimethylacrylamide (=DMAA), acrylic acid (=ACA), N-(1,1-dimethyl-3-oxoisobutyl)acrylamide (=DOBAA) and the like other than the above-mentioned ones may be used. The monomers having the hydrophilic group is represented by the following formula (16):

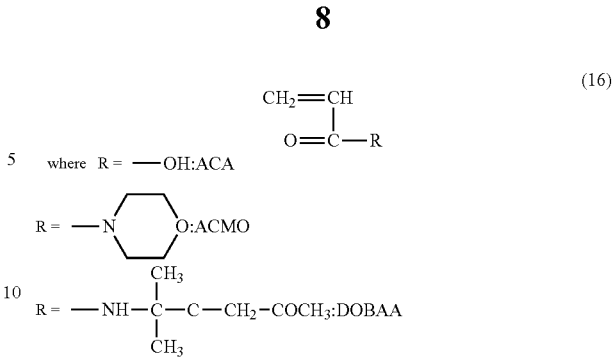

(Production Method of the Nanoparticle)

A resin (ACA) having fluoroalkyl groups at its opposite terminals in an amount of 0.6 g is dissolved in 17.6 g of ethanol. Into the solution, 1.5 g of tetraethoxysilane (Wako Pure Chemical Industries, Ltd.), 1.5 g of polydimethylsiloxane (Silaplane FM4411 produced by Chisso Corporation) and a colloidal silica (10 nm: produced by Nissan Chemical Industries, Ltd.) methanol solution are added. After stirring for a while, 1.0 g of 0.2 N aqueous ammonia is added, and stirring is made for 30 minutes.

The nanoparticle produced by the above-discussed method is contained in a PMMA (polymethylmethacrylate) film, thereby making it possible to examine a dispersibility and a surface orientation characteristics.

EXAMPLES

Hereinafter, the present invention will be discussed further in detail with reference to Example and Comparative Examples; however, the present invention is not limited to these Examples.

Example 1

Preparation of PMMA Containing Nanoparticle

A PMMA resin in an amount of 1 g was dissolved in a THF (tetrahydrofuran) solvent, and then 0.015 g of the above-mentioned nanoparticle was added while stirring was being made, followed by stirring for 30 minutes. Thereafter, cooling was made to a room temperature thereby forming a PMMA film.

Comparative Example 1

A PMMA resin in an amount of 1.49 g was dissolved in 20 ml of a THF solvent, and then 0.015 g of an oligomer was added while stirring was being made, followed by stirring for 30 minutes. Thereafter, cooling was made to a room temperature thereby forming a PMMA film.

Comparative Example 2

A PMMA resin in an amount of 1.49 g was dissolved in 20 ml of a THF solvent, and then 0.015 g of a mixture of an oligomer and a nanocomposite was added while stirring was being made, followed by stirring for 30 minutes. Thereafter, cooling was made to a room temperature thereby forming a PMMA film.

[Examination of Surface Orientation]

A contact angle measurement was conducted for the PMMA film of each Example by using dodecane, in which measurement of a contact angle for the front and back surfaces of each Example was made thereby examining a degree of surface orientation. It is meant that the number of fluoro groups becomes larger as the contact angle is larger. Results obtained are shown in Table 1.

TABLE 1

|  |  | PMMA film | | |
|---|---|---|---|---|
|  |  | Front surface | Back surface | Surface orientation |
| Example | Oligomer + Nanocomposite + Polysiloxane | 22 | 0 | ○ |
| Comparative Example 1 | Oligomer | 15 | 0 | Δ |
| Comparative Example 2 | Oligomer + Nanocomposite | 13 | 0 | Δ |

It is revealed that the dispersibility and the surface orientation characteristics are improved by causing fullerence or by-product carbon particle in production of fullerene to be included in the nanoparticle used in Example 1.

The fullerene is not limited to one of C60 and therefore may be higher order fullerenes, for example, ones of C70, C74, C76, C78, C78, C80, C82, . . . (These fullerenes follow "isolated five-ring rule").

The by-product carbon particle in production of fullerene means by-product carbon particle produced in a fullerene production method which is called a combustion method and is a carbon material which meets all properties mentioned below.

(1) Insoluble in organic solvents, and within a range of from 3 to 30° in angle of diffraction in result of an X-ray diffraction using CuKα ray, in which the most intensive peak exists within a range of 10 to 18° in angle of diffraction.

(2) Having a property of being so insoluble in organic solvents that a weight reduction of the carbon material is not more than 5% upon being subjected to a vacuum drying at 150° C. for 10 hours after 1,2,4-trimethylbenzene in an amount of 90 times by weight of the carbon material is added to the carbon material and then stirred and filtered.

(3) Having peaks at a band G 1590±20 cm$^{-1}$ and a band D 1340±40 cm$^{-1}$ in result of a Raman spectrum at an excitation wavelength of 5145 A, in which a peak intensity ratio I(D)/I(G) is within a range of 0.4 to 1.0 where peak intensities of the bands G, D are respectively I(G) and I(D).

(4) No peak exists at an angle of diffraction of 23 to 27°.

(5) Not less than 10 m$^2$/g and less than 200 m$^2$/g in specific surface area measured by a nitrogen adsorption method and less than 10% in rate of volume of pores of not larger than 10 A relative to volume of pores of not larger than 300 A.

As apparent from the above, according to the present invention, a certain organic chain which can improve the orientation characteristics to a solvent surface is introduced, thereby providing the nanoparticle which has a function of the host molecule and is capable of improving the dispersibility and the surface orientation characteristics, and the nanoparticle composite in which the guest molecule is included in the nanoparticle.

The entire contents of Japanese Patent Application No. 2006-248075, filed Sep. 13, 2006, are incorporated herein by reference.

Although the invention has been described above by reference to certain embodiments and examples of the invention, the invention is not limited to the embodiments and examples described above. Modifications and variations of the embodiments and examples described above will occur to those skilled in the art, in light of the above teachings. The scope of the invention is defined with reference to the following claims.

INDUSTRIAL USABILITY

The nanoparticle or the nanoparticle composite according to the present invention makes it possible to cause the oligomer section having the hydrophobic fluoroalkyl groups and the hydrophilic groups to be oriented on a surface, thereby realizing a coating film having a soil-resistance function if it is applied to the coating film.

Additionally, it is considered that it is applied to paints and resinous products (automotive parts, construction materials and outdoor products such as fences and the like).

What is claimed is:

1. A nanoparticle comprising a chain oligomer section having a hydrophilic group and fluoroalkyl groups respectively at its opposite terminals, a three-dimensional silica network section, and an organic chain having fluorine or silicon, and has a structure represented by the following formula (2):

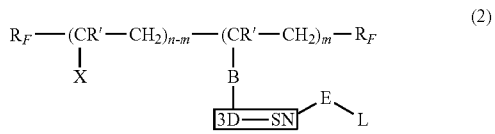

where R' is independent H or independent alkyl group; X is the hydrophilic group and is selected from the group consisting of an OH group, an NCO group, an NH$_2$ group, an NHR group (where R is alkyl group) and a COY group (where Y is a hydrophilic group); R$_F$ is the fluoroalkyl group having a carbon number of 2 to 10 and a molecular weight of 119 to 1000; 3D-SN is the three-dimensional silica network section; B is selected from the group consisting of an O, O═C—O, NH—C═O and NR—C═O (where R is alkyl group); E is O, O═C—O, NH—C═O or NR—C═O (where R is alkyl group); L is [(CH$_2$O)$_l$—[Si(CH$_3$)$_2$O]$_k$—(CH$_2$O)$_l$]-α, (CF$_2$)j-α or (CF$_2$O)$_h$-α where α is COY group (where Y is hydrophilic group), NCO group, NH$_2$ group, NHR group (R is alkyl group), R group (or alkyl group) or H; n is 1≦n≦10; m is 1≦m≦n; k is 1≦k≦500; l is 0≦l≦10; j is 0≦j≦20; and h is 1≦h≦20.

2. A nanoparticle as claimed in claim 1, wherein the chain oligomer section in the above formula (2) has a molecular weight of 252 to 100,000.

3. A nanoparticle composite comprising a host molecule which is the nanoparticle described in claim 1, and a guest molecule which is trapped by being confined in the three-dimensional structure of the host molecule.

4. A nanoparticle composite comprising a host molecule which is the nanoparticle described in claim 2, and a guest molecule which is trapped by being confined in the three-dimensional structure of the host molecule.

* * * * *